United States Patent [19]

Santilli

[11] 4,284,768
[45] Aug. 18, 1981

[54] 1,2-DIHYDRO-4-AMINO-2-OXO-3-QUINO-LINE-CARBOXYLIC ACID DERIVATIVES

[75] Inventor: Arthur A. Santilli, Havertown, Pa.

[73] Assignee: American Home Products Corporation, New York, N.Y.

[21] Appl. No.: 166,273

[22] Filed: Jul. 2, 1980

[51] Int. Cl.$^3$ .................. C07D 215/54; C07D 413/04
[52] U.S. Cl. .................................... 544/128; 544/363; 546/156
[58] Field of Search ................ 544/128, 363; 546/156

[56] References Cited

PUBLICATIONS

Mitscher et al., *J. Med. Chem.*, vol. 21 (1978), pp. 485–489.
Coppola et al., *J. Heterocyclic Chem.*, vol. 16 (1979), p. 1605.

*Primary Examiner*—Henry R. Jiles
*Assistant Examiner*—R. W. Ramsuer
*Attorney, Agent, or Firm*—Richard K. Jackson

[57] ABSTRACT

1,2-Dihydro-4-amino-2-oxo-3-quinolinecarboxylic acids, esters and amide derivatives are disclosed as antisecretory agents useful in the treatment of peptic ulcer disease.

11 Claims, No Drawings

1,2-DIHYDRO-4-AMINO-2-OXO-3-QUINOLINE-CARBOXYLIC ACID DERIVATIVES

BRIEF DESCRIPTION OF THE INVENTION

The 1,2-dihydro-4-amino-2-oxo-3-quinoline carboxylic acid derivatives disclosed herein act as gastric anti-secretory agents useful in the treatment of peptic ulcer disease. As anti-secretory agents, the compounds of this invention reduce (1) total gastric volume, (2) hydrogen ion secretion, or (3) hydrogen ion concentration. The reduction of any one of these parameters aids in relieving the debilitating effects of peptic ulcer disease in humans. The use of compounds exhibiting antisecretory activity in the curative and/or prophylactic treatment of peptic ulcer disease is an established, beneficial procedure.

DETAILED DESCRIPTION OF THE INVENTION

In accordance with this invention, there is provided a group of anti-secretory agents of the formula:

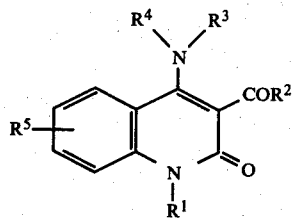

in which
 $R^1$ is hydrogen, alkyl of one to six carbon atoms, allyl or propargyl;
 $R^2$ is hydroxy, alkoxy of one to six carbon atoms, alkylamino of one to six carbon atoms, dialkylamino in which each alkyl group is of one to six carbon atoms or

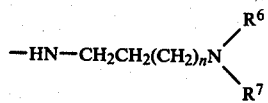

where n is 0 or 1 and $R^6$ and $R^7$ are alkyl of one to three carbon atoms; provided that when $—COR^2$ is an amide $R^3$ and $R^4$ are hydrogen;
 $R^3$ and $R^4$ are, independently, hydrogen or alkyl of one to six carbon atoms, and when taken together with the nitrogen atom to which they are attached, $R^3$ and $R^4$ form a 4-morpholinyl, 4-methyl-1-piperazinyl, or 4-(2-hydroxyethyl)-1-piperazinyl substituent; and
 $R^5$ is hydrogen, chlorine or bromine,
or a pharmaceutically acceptable salt thereof.

The compounds of this invention are prepared by reaction of isatoic anhydride, 5-chloro- or bromo-isatoic anhydride or their N-alkyl, allyl or propargyl analogues with sodium di(lower alkyl)malonate to obtain the 4-hydroxy-2-oxo-3-quinolinecarboxylic acid lower alkyl ester (Coppola et al., J. Het. Chem. 16, 1605 (1979)) followed by replacement of the 4-hydroxy substituent by chlorine or bromine by reaction with $POCl_3$ or $POBr_3$. The 4-halo-2-oxo-3-quinolinecarboxylic acid lower alkyl ester intermediates, which form an additional aspect of this invention, react smoothly with the desired mono- and di-alkyl amines as well as heterocyclic amines to yield the 4-substituted amino containing anti-secretory agents of this invention.

The 4-amino-2-oxo-3-quinoline carboxylic acid alkyl esters are prepared directly from anthranilonitrile or 5-chloro- or bromo-anthranilonitrile and sodium dialkylmalonate. The reaction product is the sodio salt of 4-amino-1,2-dihydro-2-oxo-3-quinolinecarboxylic acid alkyl ester or the corresponding 6-halo derivative, which upon acidification is converted to the 1-protonated compounds of the formula:

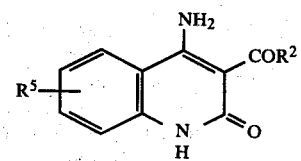

The sodio salt of the 4-amino-1,2-dihydro-2-oxo-3-quinolinecarboxylic acid alkyl esters react readily with an alkyl iodide, allyl iodide or propargyl iodide to afford the 4-amino-1-substituted products of the invention. These 4-amino-1-substituted or unsubstituted products may be diazotized in the presence of hydrochloric or hydrobromic acid to yield the corresponding 4-halo intermediates.

The 2-oxo-3-quinoline carboxylic acid amides, where $R^2$ is an amino group, are prepared conventionally from the 3-carboxylic acid esters by reaction with the desired amine.

These compounds which contain a basic amino substituent, such as the N-methyl piperazine substituted derivatives and dialkylamino alkyl amides may be converted to pharmaceutically acceptable salts with such acids as hydrochloric, hydrobromic, sulfuric, phosphoric, methane sulfonic, nitric, p-toluene sulfonic, acetic, citric, maleic, succinic acid, and the like.

The 4-halo-2-oxo-3-quinoline-carboxylic acid lower alkyl ester intermediates referred to supra, present the following structural formula:

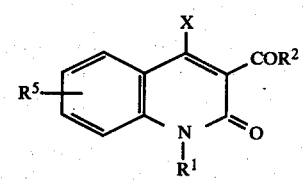

where
 $R^1$ is hydrogen, alkyl of one to six carbon atoms, allyl or propargyl;
 $R^2$ is alkoxy of one to six carbon atoms;
 $R^5$ is hydrogen, chlorine or bromine and
 X is chlorine or bromine.

The sodio salt of 4-amino-1,2-dihydro-2-oxo-3-quinolinecarboxylic acid alkyl esters referred to supra, are an additional compound intermediate aspect of this invention and are depicted in the following structural formula:

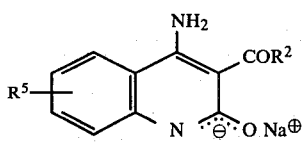

Each of the anti-secretory agents of this invention is active in the following scientifically recognized, standard test for gastric anti-secretory activity:

Male Charles River rats of Spraque-Dawley strain and 190 to 240 grams body weight are food deprived for 24 hours with water ad libitum until the test. Groups of ten rats each are assigned to either control or drug treatment. Pyloric ligation was performed under ether anesthesia through a midline laparotomy, and either control vehicle (0.25 methylcellulose) or drug in control vehicle was administered intraduodenally (i.d.). The rats are sacrificed by $CO_2$ asphyxiation four hours after pyloric ligation. The stomachs are removed and the gastric contents emptied into graduated centrifuge tubes. The gastric samples are centrifuged for 20 minutes and those obviously contaminated by food, blood or feces are discarded. The volume of gastric fluid is recorded and the acid concentration of 1.0 milliliter sample aliquots is measured by electrometric titration to pH 7.0 with 0.1 N NaOH. The calculated product of gastric volume (ml/4 hr) and acid concentration (mEq/L) estimates the total acid output (TAO, mEq/4 hr) over the four hour test period. An analysis of variance is performed on these data to determine statistically significant ($p<0.05$) deviation between control versus drug-treated groups.

Thus, the compounds of this invention are useful in the treatment of peptic ulcer disease. The dosage regimen will vary with the mode of administration, size and age of the subject treated and with the severity of the condition being treated. Thus, administration of the anti-secretory agents disclosed and claimed herein must be under the guidance and instruction of a physician for optimization of individual treatment.

The compounds of this invention may be administered by conventional oral or parenteral routes as solids, liquids or nebulized suspensions. Conventional adjuvants known to the art may be combined with the anti-secretory agents of this invention to provide compositions and solutions for administrative purposes, although it is considered desirable and feasible to use neat or pure compounds without additives other than for the purpose of providing suitable pharmaceutically acceptable solution or liquid or vapor suspensions.

The following examples are presented to illustrate the production of representative compounds of this invention. After each example, the anti-secretory activity expressed as the percent inhibition of gastric total acid output at a dose of 32 milligrams per kilogram intraduodenal (i.d.) is presented for the exemplified compound.

EXAMPLE 1

1,2-Dihydro-1-methyl-4-(4-methyl-1-piperazinyl)-2-oxo-3-quinolinecarboxylic acid ethyl ester To a solution containing 2.3 g. of sodium in 200 ml. of ethanol was added 16.0 g. of diethyl malonate. The reaction mixture was stirred for a few minutes and taken to dryness in a rotary evaporator. The ethanol was replaced with 200 ml. of DMF. N-Methylisatoic anhydride (17.7 g.) was added to the reaction mixture which was then heated under reflux with stirring for 1 hour. The reaction mixture was then cooled to room temperature and poured into 1-liter of water. The resulting precipitate amounted to 13.1 g. of 1,2-dihydro-4-hydroxy-1-methyl-2-oxo-3-quinolinecarboxylic acid ethyl ester, m.p. 100°–102° C.

A mixture of 6.7 g. of 1,2-dihydro-4-hydroxy-1-methyl-2-oxo-3-quinolinecarboxylic acid ethyl ester in 50 ml. of phosphorus oxychloride was heated under reflux for 2 hours. The excess phosphorus oxychloride was removed in vacuo on a rotary evaporator. Ice and water were added to the oily residue. The product solidified on scratching. Recrystallization from ethanol-petroleum ether gave m.p. 94°–96° C.

Analysis for: $C_{13}H_{12}ClNO_3 \cdot \frac{1}{2}H_2O$: Calculated: C, 57.46; H, 4.70; N, 5.15. Found: C, 57.59; H, 4.45; N, 5.21.

A stirred mixture of 9.5 g. of 4-chloro-1,2-dihydro-1-methyl-2-oxo-3-quinolinecarboxylic acid ethyl ester, 3.6 g. of N-methylpiperazine and 3.8 g. of sodium carbonate in 50 ml. of ethanol was heated under reflux for 3 hours and filtered. The filtrate was taken to dryness on a rotary evaporator leaving a thick, tarry oily residue. On triturating the oil with diethyl ether, there was obtained 9.4 g. of impure title compound, m.p. 144°–148° C. Recrystallization from ethanol gave 5.5 g. of the title compound, m.p. 154°–156° C.

Analysis for: $C_{18}H_{23}N_3O_3$: Calculated: C, 65.63; H, 7.04; N, 12.76. Found: C, 65.14; H, 7.14; N, 12.72.

81% inhibition at 32 mg/kg, i.d.

EXAMPLE 2

4-Amino-1-ethyl-1,2-dihydro-2-oxo-3-quinolinecarboxylic acid ethyl ester

To 500 ml. of ethanol containing 6.9 g. (0.3 g. atoms) of sodium was added 48.09 (0.3 mole) of diethyl malonate. After a few minutes 17.7 g. (0.15 mole) of anthranilonitrile was added. The reaction mixture was heated with stirring for 5½ hours during which time the sodio salt of 4-amino-1,2-dihydro-2-oxo-3-quinolinecarboxylic acid ethyl ester was deposited. The sodio salt was removed by filtration. The sodium salt was placed in 500 ml. of water and the reaction acidified with glacial acetic acid. The resulting precipitate was collected on a filter under suction. The product, 4-amino-1,2-dihydro-2-oxo-3-quinolinecarboxylic acid ethyl ester amounted to 6.8 g. Recrystallization from ethanol gave 6.3 g. m.p. 248°–250° C.

Analysis for: $C_{12}H_{12}N_2O_3$: Calculated: C, 62.06; H, 5.21; N, 12.06. Found: C, 62.15; H, 5.21; N, 12.34.

A solution of 7.6 g. (0.03 mole) of this sodium salt was dissolved in 50 ml. of dimethyl formamide. To this solution was added 6.2 g. (0.14 mole) of ethyl iodide. The reaction mixture was heated on a steam bath for ½ hour. The reaction mixture was cooled in ice and poured into 500 ml. of water. The resulting precipitate was collected on a filter. The product amounted to 5.5 g. Recrystallization from ethanol afforded 3.5 g. of pure product, m.p. 200°–201° C.

Analysis for: $C_{14}H_{16}N_2O_3$: Calculated: C, 64.60; H, 6.20; N, 10.76. Found: C, 64.20; H, 6.25; N, 10.76.

54% inhibition at 32 mg/kg, i.d.

EXAMPLE 3

4-Amino-1,2-dihydro-2-oxo-1-(2-propenyl)-3-quinolinecarboxylic acid ethyl ester

To a solution containing 7.6 g. (0.03 mole) of the sodium salt of 4-amino-1,2-dihydro-2-oxo-3- quinolinecarboxylic acid ethyl ester in 50 ml. of dimethylformamide was added 4.8 g. (0.04 mole) of allyl bromide. The reaction mixture was heated on a steam bath for ½ hour. The reaction mixture was cooled in ice and poured into 500 ml. of water. The resulting precipitate was collected on a filter and recrystallized from ethyl acetate-petroleum ether giving 4.6 g. of product, m.p. 132°–134° C.

Analysis for: $C_{15}H_{16}N_2O_3$: Calculated: C, 66.16; H, 5.92; N, 10.29. Found: C, 66.07; H, 5.96; N, 10.47.

78% inhibition at 32 mg/kg, i.d.

EXAMPLE 4

6-Chloro-1,2-dihydro-1-methyl-4-(4-methyl-1-piperazinyl)-2-oxo-3-quinolinecarboxylic acid ethyl ester To a solution containing 2.3 g. of sodium in 250 ml. of ethanol was added 16.02 g. of diethyl malonate. The ethanol was removed on a rotary evaporator. The solvent was replaced with 250 ml. of dimethyl formamide. 5-Chloro-N-methylisatoic anhydride (21.2 g.) was added and the reaction mixture was heated under reflux for 1 hour. The reaction mixture was then cooled to room temperature and poured into 1-liter of water. There was obtained 22.4 g. of product. Recrystallization from ethanol gave 6-Chloro-1,2-dihydro-4-hydroxy-1-methyl-2-oxo-3-quinolinecarboxylic acid ethyl ester, m.p. 141°–143° C.

A solution of 4.4 g. of 6-chloro-1,2-dihydro-4-hydroxy-1-methyl-2-oxo-3-quinolinecarboxylic acid ethyl ester in 50 ml. of phosphorus oxychloride was heated under reflux for 3 hours. The excess phosphorus oxychloride was removed in a rotary evaporator. Water was added to the residue giving 3.8 g. of 4,6-dichloro-1,2-dihydro-1-methyl-2-oxo-3-quinolinecarboxylic acid ethyl ester, m.p. 140°–142° C.

A mixture containing 7.1 g. of 4,6-dichloro-1-methyl-2-oxo-3-quinolinecarboxylic acid ethyl ester, 2.36 g. of N-methylpiperazine and 2.5 g. of sodium carbonate in 25 ml. of dimethyl formamide was heated under reflux with stirring for 2 hours. The reaction mixture was cooled in ice and the resulting precipitate collected. Recrystallization from ethanol gave 4.2 g. of the title compound, m.p. 163°–165° C.

Analysis for: $C_{18}H_{22}ClN_3O_3$: Calculated: C, 59.42; H, 6.09; N, 11.55. Found: C, 59.22; H, 6.00; N, 11.58.

94% inhibition at 32 mg/kg, i.d.

EXAMPLE 5

6-Chloro-1,2-dihydro-4-[4-(2-hydroxyethyl)-1-piperazinyl]-2-oxo-3-quinolinecarboxylic acid ethyl ester A stirred mixture of 6.09 g. of 4,6-dichloro-1,2-dihydro-1-methyl-2-oxo-3-quinolinecarboxylic acid ethyl ester (prepared as in Example 4), 2.12 g. of sodium carbonate, and 2.6 g. of N-2-hydroxyethylpiperazine in 50 ml. of ethanol was heated under reflux for 3 hours. The reaction mixture was filtered under suction and the filtrate taken to dryness in a rotary evaporator. On triturating the residual oil with diethyl ether gave 6.0 g. of product, m.p. 130°–134° C. Recrystallization from ethyl acetate gave 4.4 g. of the title compound, m.p. 135°–138° C.

Analysis for: $C_{19}H_{24}ClN_3O_4$: Calculated: C, 57.94; H, 6.14; N, 10.67. Found: C, 57.56; H, 6.32; N, 10.73.

EXAMPLE 6

6-Chloro-1,2-dihydro-1-methyl-4-(4-morpholinyl)-2-oxo-3-quinolinecarboxylic acid ethyl ester A solution of 200 mg. of 4,6-dichloro-1,2-dihydro-1-methyl-2-oxo-3-quinolinecarboxylic acid ethyl ester, (prepared in Example 4) in 1 ml. of morpholine was heated in a test tube for a few minutes and then was poured into 40 ml. of water. The resulting precipitate was collected and washed with water. Recrystallization from ethanol gave the title compound with m.p. 167°–169° C.

Analysis for: $C_{17}H_{19}ClN_2O_4$: Calculated: C, 58.21; H, 5.46; N, 7.98. Found: C, 58.10; H, 5.49; N, 7.97.

54% inhibition at 32 mg/kg, i.d.

EXAMPLE 7

1-Allyl-4-amino-6-chloro-1,2-dihydro-2-oxo-3-quinolinecarboxylic acid ethyl ester To a solution of 6.9 g. (0.3 g. atom) of sodium in 500 ml. of ethanol was added 48 g. (0.3 mole) of diethyl malonate. The reaction mixture was stirred for a few minutes and 15.2 g. (0.1 mole) of 2-amino-5-chlorobenzonitrile was added. The reaction mixture was heated under reflux with stirring for 5 hours during which time the sodio salt of the product precipitated out of solution. The reaction mixture was cooled in ice and filtered. The sodio salt amounted to 31.3 g. A seven gram sample was placed into 100 ml. of water and acidified with conc. hydrochloric acid. There was obtained 4.6 g. of solid product, m.p. 292°–294° C. Recrystallization from dimethyl formamide-water gave 4 g. of 4-amino-6-chloro-1,2-dihydro-2-oxo-3-quinolinecarboxylic acid ethyl ester, m.p. 293°–294° C.

Analysis for: $C_{12}H_{11}ClN_2O_3$: Calculated: C, 54.04; H, 4.16; N, 10.51. Found: C, 53.77; H, 4.16; N, 10.29.

To a solution of 8.66 g. (0.03 mole) of the sodium salt of 4-amino-6-chloro-1,2-dihydro-2-oxo-3-quinolinecarboxylic acid ethyl ester in 50 ml. of dimethyl formamide was added 4.84 g. (0.04 mole) of allyl bromide. The reaction mixture was heated on a steam bath for 2 hours and was then cooled to room temperature. The reaction mixture was poured into 500 ml. of water. The reaction mixture was allowed to stand for several hours at room temperature and was then filtered. There was obtained 7.6 g. of product. Recrystallization from ethyl acetate gave 3.4 g. of product, m.p. 144°–146° C.

Analysis for: $C_{15}H_{15}ClN_2O_3$: Calculated: C, 58.73; H, 4.93; N, 9.13. Found: C, 58.39; H, 4.97; N, 9.12.

EXAMPLE 8

4-Amino-N-(2-diethylaminoethyl)-1-ethyl-1,2-dihydro-2-oxo-3-quinolinecarboxamide The product of Example 2 is allowed to react with an excess of 2-diethylaminoethylamine, neat, under reflux conditions for several hours. The reaction mixture is cooled and poured into an excess of water to dissolve the excess 2-diethylaminoethylamine present. The title compound precipitates, is recovered by filtration and purified by recrystallization.

What is claimed is:

1. A compound of the formula:

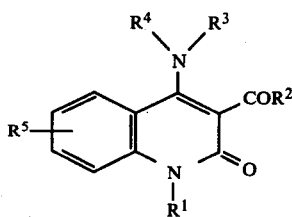

in which

R[1] is hydrogen, alkyl of one to six carbon atoms, alkyl or propargyl;

R[2] is hydroxy, alkoxy of one to six carbon atoms, alkylamino of one to six carbon atoms, dialkylamine in which each alkyl group is of one to six carbon atoms or

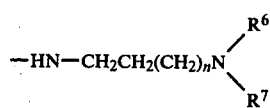

wherein n is 0 or 1 and R[6] and R[7] are alkyl of one to three carbon atoms provided that when —COR[2] is an amide R[3] and R[4] are hydrogen;

R[3] and R[4] are, independently hydrogen or alkyl of one to six carbon atoms, and when taken together with the nitrogen atom to which they are attached, R[3] and R[4] form a 4-morpholinyl, 4-methyl-1-piperazinyl or 4-(2-hydroxyethyl)-1-piperazinyl substituent, and R[5] is hydrogen, chlorine or bromine, or a pharmaceutically acceptable salt thereof.

2. The compound of claim 1 which is 1,2-dihydro-1-methyl-4-(4-methyl-1-piperazinyl)-2-oxo-3-quinolinecarboxylic acid ethyl ester or a pharmaceutically acceptable salt thereof.

3. The compound of claim 1 which is 4-amino-1,2-dihydro-1-ethyl-2-oxo-3-quinolinecarboxylic acid ethyl ester.

4. The compound of claim 1 which is 1-allyl-4-amino-1,2-dihydro-2-oxo-3-quinolinecarboxylic acid ethyl ester.

5. The compound of claim 1 which is 6-chloro-1,2-dihydro-1-methyl-4-(4-methyl-1-piperazinyl)-2-oxo-3-quinolinecarboxylic acid ethyl ester or a pharmaceutically acceptable salt thereof.

6. The compound of claim 1 which is 6-chloro-1,2-dihydro-4-[4-(2-hydroxyethyl)-1-piperazinyl]-2-oxo-3-quinolinecarboxylic acid ethyl ester or a pharmaceutically acceptable salt thereof.

7. The compound of claim 1 which is 6-chloro-1,2-dihydro-1-methyl-4-(4-morpholinyl)-2-oxo-3-quinolinecarboxylic acid ethyl ester.

8. The compound of claim 1 which is 1-allyl-4-amino-6-chloro-1,2-dihydro-2-oxo-3-quinolinecarboxylic acid ethyl ester.

9. The compound of claim 1 which is 4-amino-N-(2-diethylaminoethyl)-1-ethyl-1,2-dihydro-2-oxo-3-quinolinecarboxamide.

10. The sodium salt of 4-amino-1,2-dihydro-2-oxo-3-quinolinecarboxylic acid alkyl ester in which said alkyl group contains from one to six carbon atoms.

11. The sodium salt of 4-amino-6-chloro-1,2-dihydro-2-oxo-3-quinolinecarboxylic acid alkyl ester in which said alkyl group contains from one to six carbon atoms.

* * * * *